United States Patent [19]  [11] 4,305,946
Ehrenfreund  [45] Dec. 15, 1981

[54] PROPARGYL THIO-NITRO-PYRIDINES

[75] Inventor: Josef Ehrenfreund, Allschwil, Switzerland

[73] Assignee: Ciba-Geigy Corporation, Ardsley, N.Y.

[21] Appl. No.: 166,678

[22] Filed: Jul. 7, 1980

[30] Foreign Application Priority Data

Jul. 11, 1979 [CH] Switzerland .................. 6476/79

[51] Int. Cl.³ .................. C07D 213/61; A01N 43/40
[52] U.S. Cl. .................................. 424/263; 546/297
[58] Field of Search .................. 546/297; 424/263

[56] References Cited
U.S. PATENT DOCUMENTS 2,922,793  1/1960  Rockett ........................... 546/290
4,170,704  10/1979  Brandman et al. ............... 546/297

OTHER PUBLICATIONS

Klingsberg, Pyridine and its Derivatives, Part Four, pp. 354 & 358, Interscience Publishers, (1964).

Primary Examiner—Alan L. Rotman
Attorney, Agent, or Firm—Frederick H. Rabin

[57] ABSTRACT

Novel propargylthio-nitropyridines of the formula

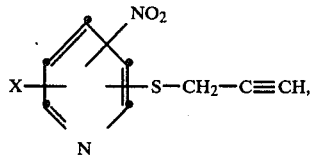

wherein X is hydrogen or halogen, processes for producing these compounds, as well as compositions containing them, for use in combating pests, particularly for use as ovicides for combating insect pests which do damage by eating, in the field of plant protection.

10 Claims, No Drawings

PROPARGYL THIO-NITRO-PYRIDINES

The present invention relates to novel propargylthionitropyridines, to processes for producing them, and to their use in the control of pests.

The propargylthio-nitropyridines according to the invention have the formula I

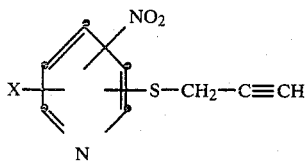

wherein X is hydrogen or halogen.

Compounds of the formula I which are preferred according to the invention on account of their activity as pesticidal active substances are those wherein the propargylthio group is in the 2-position. To be emphasised are moreover those compounds of the formula I wherein X is hydrogen or chlorine. Particularly valuable compounds of the formula I by virtue of their biological effectiveness are those wherein the nitro group is in the 3- or 5-position and X is hydrogen.

The compounds of the formula I can be produced by methods analogous to methods known per se, such as those customary for S-alkylations of aromatic and heteroaromatic thiols.

Thus, for example, a compound of the formula I can be obtained by reaction of a pyridinethiol of the formula II

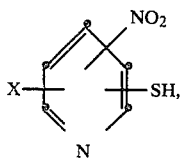

in the presence of an acid acceptor, with a propargyl halide of the formula III

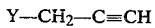

In the above formulae II and III, the radical X has the meaning defined under the formula I, and Y is halogen, preferably chlorine or bromine.

The aforementioned process is preferably performed under normal pressure, and in the presence of an organic solvent or diluent. Suitable solvents or diluents are for example: alcohols, especially lower alcohols, such as methanol, ethanol, propanols, and so forth; ethers and ethereal compounds, such as diethyl ether, dipropyl ether, dibutyl ether, dioxane, dimethoxyethane and tetrahydrofuran; N,N-dialkylated carboxylic acid amides; aliphatic and aromatic hydrocarbons, for example benzene, toluene and xylene; dimethyl sulfoxide, as well as ketones, for example acetone, methyl ethyl ketone, methyl isopropyl ketone and methyl isobutyl ketone. The process is generally performed at a temperature of 0° to 150° C., preferably between 25° and 125° C., in the presence of an acid acceptor. Suitable acid acceptors are inorganic bases, such as $K_2CO_3$, $Na_2CO_3$, $CaCO_3$ and appropriate hydrogen carbonates, or organic bases, for example tertiary amines, such as triethylamine.

The starting materials of the formulae II and III are known, or they can be produced by processes analogous to known processes. Thus, for example, compounds of the formula II and the production thereof are described in the following publications: J. Pharm. Soc. Jap. 64, 201 (1944); J. Am. Chem. Soc. 62, 1697 (1940); Yakugaku Zasshi 78, 417 (1958) and German Patent Specification No. 1,014,375.

The use of unsaturated ethers for combating ectoparasites, for example ticks, mites and vectors, is known from the Swiss Patent Specification No. 528,210. The substituted phenylpropargyl ethers listed therein have however only a limited value for use as insecticides.

It has now been found that surprisingly the compounds of the formula I according to the invention, whilst having high tolerance to plants and negligible toxicity to warmblooded animals, have excellent activity as pesticidal active substances, particularly for combating insects which infest plants.

The compounds of the formula I are excellently suitable for combating for example insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae.

The compounds of the formula I are characterised in particular by a broad ovicidal and ovolarvicidal action, which extends to eggs and sets of eggs of insect pests. To be particularly emphasised in this respect is the effectiveness of the compounds according to the invention against representatives of the order Lepidoptera, especially of the family Noctuidae. The compounds of the formula I can therefore be used also for combating insects which damage plants by eating, in crops of ornamental plants and productive plants, especially in cotton crops (for example against Spodoptera littoralis and Heliothis virescens).

The action of the compounds according to the invention and of the compositions containing them can be considerably broadened and adapted to suit given circumstances by the addition of other insecticides and/or acaricides. Suitable as additives are for example the following active substances: organic phosphorus compounds, nitrophenols and derivatives thereof, pyrethroids, formamidines, ureas, carbamates and chlorinated hydrocarbons.

The compounds of the formula I can be combined with particular advantage also with substances having a pesticidally intensifying effect. Examples of such compounds are, inter alia: piperonylbutoxide, propionyl ethers, propionyl oximes, propynyl ethers, propynyl oximes, propynyl carbamates and propynyl phosphonates, 2-(3,4-methylenedioxyphenoxy)-3,6,9-trioxaundecane or S,S,S-tributylphosphorotrithionates.

The compounds of the formula I can be used on their own or together with suitable carriers and/or additives. Suitable carriers and additives may be solid or liquid and correspond to the substances common in formulation practice, such as natural and regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations: dusts, scattering agents or granulates (coated granules, impregnated granules and homogeneous granules);

liquid preparations:

(a) water-dispersible concentrates of active substance: wettable powders, pastes or emulsions;

(b) solutions.

The content of active substance in the described compositions is between 0.1 and 95%.

The active substances of the formula I can be formulated for example as follows:

Dusts

The following substances are used to produce (a) a 5% dust and (b) a 2% dust:

(a)

5 parts of active substance, and
95 parts of talcum; and (b)

2 parts of active substance,
1 part of highly dispersed silicic acid, and
97 parts of talcum.

The active substance is mixed and ground with the carriers.

Granulate

The following ingredients are used to produce a 5% granulate:

5 parts of active substance,
0.25 part of epoxidised vegetable oil,
0.25 part of cetyl polyglycol ether,
3.50 parts of polyethylene glycol, and
91 parts of kaolin (particle size 0.3–0.8 mm).

The active substance is mixed with the epoxidised vegetable oil and dissolved in 6 parts of acetone, and the polyethylene glycol and cetyl polyglycol ether are then added. The solution obtained is sprayed onto kaolin and the acetone is subsequently evaporated off in vacuo.

Wettable powders

The following constituents are used to produce: (a) a 40% wettable powder, (b) and (c) a 25% wettable powder, and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminum silicate,
16.5 parts of kieselgur, and
46 parts of kaolin; and (d)

10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkyl-
40 parts of dimethylformamide, and
43.2 parts of xylene;

(b)

25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene;

(c)

50 parts of active substance,
4.2 parts of tributylphenol-polyglycol ether,
5.8 parts of calcium-dodecylbenzenesulfonate,
20 parts of cyclohexanone, and
20 parts of xylene.

Emulsions of the concentration required can be prepared from these concentrates by dilution with water.

Sprays

The following constituents are used to produce (a) a 5% spray and (b) a 95% spray:

(a)

5 parts of active substance,
1 part of epoxidised vegetable oil,
94 parts of ligroin (boiling limits 160°–190° C.); and (b)

95 parts of active substance, and
5 parts of epoxidised vegetable oil.

EXAMPLE 1

7 g of 5-nitro-pyridine-2-thiol are suspended in acetone, and 5 g of potassium carbonate are added. There are then added 6 g of 3-bromopropine-1, and, after the exothermic reaction has finished, the reaction mixture is refluxed for about 30 minutes. The solution obtained is poured onto ice, and the precipitate occurring is filtered off. The crude product is purified by recrystallisation from methanol to yield 2-propargylthio-5-nitropyridine, m.p. 98°–99.5° C.

The following compounds embraced by the formula I are produced by a procedure analogous to that described above:

2-propargylthio-3-nitropyridine, m.p. 119°–121° C.;
2-propargylthio-3-nitro-5-chloropyridine, m.p. 82°–84° C.;
2-propargylthio-3-chloro-5-nitropyridine, m.p. 143°–146° C.;
2-nitro-5-propargylthiopyridine.

EXAMPLE 2

Ovicidal action against Heliothis virescens and Spodoptera littoralis

Appropriate proportions of a wettable pulverulent formulation containing 25 percent by weight of the active substance to be tested were in each case diluted with water in such amounts that aqueous emulsions of increasing concentration of active substances were obtained.

Into these emulsions containing active substance were immersed for 3 minutes one-day-old sets of eggs, deposited on absorbent paper, of Heliothis and Spodoptera, respectively, and they were then filtered off on round filters with suction. After drying, the sets of eggs treated in this manner were laid out in Petri dishes and kept at 28° C. in darkness. After about 4 days, the hatching rate was determined and compared with that of untreated control specimens. The minimum concentration of active substance required for a 100% mortality of the eggs was taken as a basis for the evaluation.

The compounds according to Example 1 exhibited in this test a good ovicidal action against the pests on which the test was made.

EXAMPLE 3

Action against *Aedes Aegypti*

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 two-day-old Aëdes larvae were placed into each container. The mortality rate was ascertained after 1, 2 and 5 days, respectively.

Compounds according to Example 1 exhibited in this test a good action against *Aeedes aegypti*.

EXAMPLE 4

Action against *Laspeyresia pomonella* (eggs)

Deposited eggs of *Laspeyresia pomonella*, which were not older than 24 hours, were immersed on filter paper for 1 minute in an acetonic-aqueous solution containing 400 ppm of the active substance to be tested. After the solution had been dried off, the eggs were transferred to Petri dishes and kept at a temperature of 28° C. After 6 days, the percentage rate of hatching from the treated eggs was determined.

Compounds according to Example 1 exhibited a good action in the above test.

What is claimed is:

1. A compound of the formula I

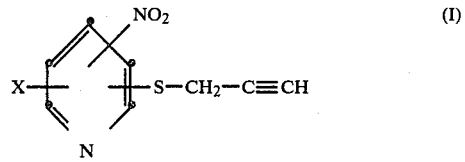

wherein X is hydrogen or halogen.

2. A compound according to claim 1, wherein the propargylthio group is in the 2-position.

3. A compound according to claim 1 or 2, wherein X is hydrogen or chlorine.

4. A compound according to claim 1 or 2, wherein the nitro group is in the 3- or the 5-position, and X is hydrogen.

5. The compound according to claim 2 of the formula

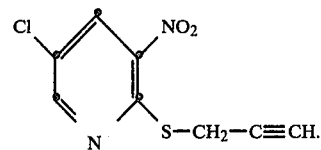

6. The compound according to claim 2 of the formula

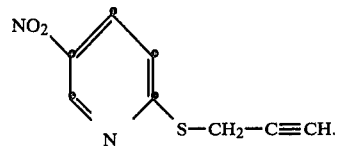

7. The compound according to claim 2 of the formula

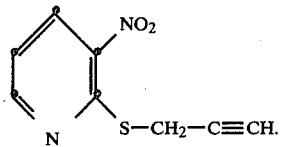

8. An insecicidal composition comprising (1) as active ingredient an insecticidally effective amount of a compound according to claims 1 or 2, and (2) an inert carrier.

9. A method for combatting insects which comprises applying thereto an insecticidally effective amount of a compound according to claim 1 or 2.

10. A method according to claim 9 in which the compound is applied to eggs of insects of the family Noctuidae.

* * * * *